(12) United States Patent
Deprez et al.

(10) Patent No.: US 6,420,341 B1
(45) Date of Patent: Jul. 16, 2002

(54) SULPHUR DERIVATIVES WITH A RETROAMIDE BOND AS ENDOTHELIN-CONVERTING ENZYME INHIBITORS

(75) Inventors: Pierre Deprez, Thiais; Jacques Dumas, Neuilly Plaisance; Jacques Guillaume, Livry Gargan, all of (FR)

(73) Assignee: Aventis Pharma S.A. (FR)

( * ) Notice: Subject to any disclaimer, the term of this patent is extended or adjusted under 35 U.S.C. 154(b) by 0 days.

(21) Appl. No.: 09/142,288

(22) PCT Filed: Mar. 3, 1997

(86) PCT No.: PCT/FR97/00369
§ 371 (c)(1),
(2), (4) Date: Oct. 30, 1998

(87) PCT Pub. No.: WO97/32849
PCT Pub. Date: Sep. 12, 1997

(30) Foreign Application Priority Data

Mar. 4, 1996 (FR) ............................................ 96 02674

(51) Int. Cl.$^7$ .............................................. A61K 38/00
(52) U.S. Cl. ........................................................ 514/19
(58) Field of Search ........................................... 514/19

(56) References Cited

FOREIGN PATENT DOCUMENTS

| DE | 3819539 | 12/1988 |
|----|---------|---------|
| EP | 0161769 | 11/1985 |
| EP | 0460679 | 12/1991 |
| EP | 0636621 | 2/1995  |

OTHER PUBLICATIONS

Pham et al, "Effects . . . Hypertension", J. Pharmacol. Exp. Ther., vol. 265, No. 3, 1993, XP 000604484, pp. 1339–1347.
Fournie–Zaluski et al, "1H . . . Recognition", Journal of Medical Chemistry, vol. 29, No. 5, 1986 XP002016433, pp. 751–757.
Higashiura et al, "Preparation . . . Stimulators", Chemical Abstracts Registry Handbook, Number Section, 1992, Abstract No. 70336.
Luly et al, "Modified . . . Renin", Chemical Abstracts Registry Handbook, Number Section, 1987 Abstract No. 89295y.
Kukola, "Optimization . . . Enzyme", Bioorganic & Medicinal Chemistry Letters, vol. 6, No. 6, Mar. 13, 1996 XP000604549, pp. 619–624.

*Primary Examiner*—Zohreh Fay
(74) *Attorney, Agent, or Firm*—Bierman, Muserlian and Lucas

(57) ABSTRACT

Products of formula (1), wherein $R_1$ is particularly phonyl or biphenyl optionally substituted by halogen n1 and n2 are 0 or 1, $R_2$ is particularly hydrogen or methyl substituted by phenyl, which may in turn be substituted, and A is partcularly carboxy or alkyl substituted particularly by phenoxy, as well as all isomers and organic and inorganic base addition salts therof, are disclosed.

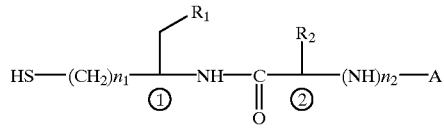

(I)

3 Claims, No Drawings

SULPHUR DERIVATIVES WITH A RETROAMIDE BOND AS ENDOTHELIN-CONVERTING ENZYME INHIBITORS

The present invention relates to new sulphur derivatives containing a retroamide bond, their preparation process, the new intermediates obtained, their use as medicaments, the pharmaceutical compositions containing them and the new use of such derivatives.

A subject of the present invention is the products of formula (I):

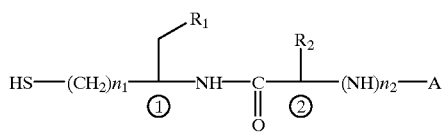

in which:
- $R_1$ represents an phenyl or biphenyl radical optionally substituted by one or more radicals chosen from halogen atoms, the following radicals: optionally protected hydroxyl, linear or branched alkoxy containing up to 4 carbon atoms, cyano, free, salified, esterified or amidified carboxy, benzyloxy and the dioxol radical, n1 and n2, identical or different, represent the integer 0 or 1,
- $R_2$ represents a hydrogen atom or a methyl radical substituted by a phenyl, phenylthio or indolyl radical and optionally by a second phenyl radical, these phenyl, phenylthio and indolyl radicals being optionally substituted by one or more radicals chosen from halogen atoms and the following radicals: optionally protected hydroxyl, linear or branched alkoxy containing up to 4 carbon atoms, cyano, free, salified, esterified or amidified carboxy, benzyloxy, thienyl, naphthyl and phenyl, these three last radicals being themselves optionally substituted by one or more radicals chosen from halogen atoms and the following radicals: optionally protected hydroxyl, linear or branched alkoxy containing up to 4 carbon atoms, cyano and free, salified, esterified or amidified carboxy,
- A represents the free, salified, esterified or amidified carboxy radical, the free or salified tetrazolyl radical, or an alkyl radical, containing up to 10 carbon atoms and substituted by a radical chosen from the following radicals: free, salified, esterified or amidified carboxy, the optionally protected hydroxyl, alkoxy containing up to 4 carbon atoms, phenoxy, phenyl, naphthyl, thienyl, indolyl and pyridyl, these radicals being optionally substituted by one or more radicals chosen from halogen atoms and the following radicals: optionally protected hydroxyl, linear or branched alkoxy containing up to 4 carbon atoms, cyano and free, salified, esterified or amidified carboxy,
- 1 and 2 indicating, if appropriate, the asymmetric centres of the products of formula (I), said products of formula (I) being in all possible racemic, enantiomeric and diastereoisomeric isomer forms, as well as the addition salts with mineral and organic acids or with the mineral and organic bases of said products of formula (1).

In the products of formula (I) and in what follows:
- the term linear or branched alkyl radical designates the following radicals: methyl, ethyl, propyl, isopropyl, butyl, isobutyl, sec-butyl, tert-butyl, pentyl, isopentyl, hexyl, isohexyl and also heptyl, octyl, nonyl and decyl as well as their linear or branched position isomers,
- the term linear or branched alkoxy radical designates the following radicals: methoxy, ethoxy, propoxy, isopropoxy, linear, secondary or tertiary butoxy, pentoxy or hexoxy as well as their linear or branched position isomers,
- the term halogen atom preferably designates the chlorine atom, but can also represent a fluorine, bromine or iodine atom.

The hydroxyl radical can in particular be in the form of the trifluoromethylsulphonyloxy radical.

The carboxy radical or radicals of the products of formula (I) can be salified or esterified by the various groups known to a person skilled in the art among which there can be mentioned, for example:
- among the salification compounds, mineral bases such as, for example, an equivalent of sodium, of potassium, of lithium, of calcium, of magnesium or of ammonium or organic bases such as, for example, methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methyl-glucamine.

The sodium or potassium salts are preferred,
- among the esterification compounds, the alkyl radical in order to form alkoxy carbonyl or arylalkoxycarbonyl groups, such as, for example, methoxycarbonyl, ethoxycarbonyl, n-propoxy- and isopropoxy-carbonyl, n-butoxy-, isobutoxy- and tert-butoxy-carbonyl or benzyloxycarbonyl, these alkyl radicals can be substituted by radicals chosen for example from halogen atoms, hydroxyl, alkoxy, acyl, acyloxy, alkylthio, amino or aryl radicals such as, for example, in the chloromethyl, hydroxypropyl, methoxymethyl, propionyloxymethyl, methylthiomethyl, dimethylaminoethyl, benzyl or phenethyl groups.

There can also be mentioned the radicals formed with the remainders of easily cleavable esters such as the methoxymethyl, ethoxymethyl radicals; the acyloxyalkyl radicals such as pivaloyloxymethyl, pivaloyloxyethyl, acetoxymethyl or acetoxyethyl; the alkyloxycarbonyloxy alkyl radicals such as methoxycarbonyloxy methyl or ethyl radicals, the isopropyloxycarbonyloxy methyl or ethyl radicals.

A list of such ester radicals can be found for example in the European Patent EP 0 034 536.

By amidified carboxy is meant the groups of —CON($R_6$) ($R_7$) type in which the identical or different $R_6$ and $R_7$ radicals represent a hydrogen atom or an alkyl radical having from 1 to 4 carbon atoms such as the methyl, ethyl, propyl, isopropyl, butyl, isobutyl, sec-butyl or tert-butyl radicals.

Among the —CON($R_6$) ($R_7$) groups defined above, those in which the —N($R_6$) ($R_7$) radical represents the amino, mono or dimethylamino radical are preferred.

The N($R_6$) ($R_7$) radical can also represent a heterocycle which may or may not contain an additional heteroatom. There can be mentioned the pyrrolyl, imidazolyl, indolyl, piperidino, morpholino, piperazinyl radicals. The piperidino or morpholino radicals are preferred.

Examples of the protective group of the protected hydroxyl radical are given in particular in the usual book known to a person skilled in the art: Protective Groups in Organic Synthesis, Theodora W. Greene, Harvard University, printed in 1981 by Wiley-Interscience Publishers, John Wiley & Sons.

The addition salts with mineral or organic acids of the products of formula (I) can be, for example, the salts formed with the following acids: hydrochloric, hydrobromic, hydroiodic, nitric, sulphuric, phosphoric, propionic, acetic, formic, benzoic, maleic, fumaric, succinic, tartaric, citric, oxalic, glyoxylic, aspartic, ascorbic, alkylmonosulphonic acids such as for example methanesulphonic acid, ethanesulphonic acid, propanesulphonic acid, alkyldisulphonic acids such as for example methanedisulphonic acid, alpha, beta-ethanedisulphonic acid, arylmonosulphonic acids such as benzenesulphonic acid and aryldisulphonic acids.

More particularly there can be mentioned the salts formed with hydrochloric or methanesulphonic acids for example.

It should be remembered that the stereoisomerism can be defined in its widest sense as the isomerism of compounds having the same structural formulae, but the different groups of which are arranged differently in space.

It is understood that the definition of the products of formula (I) as defined above includes all possible stereoisomers, all racemic modifications, all optical isomers and all mixtures of these products which would have the activity indicated hereafter.

The products of formula (I) contain in particular two centres ①  and ②, ① being asymmetrical and ② being asymmetrical when $R_2$ does not represent a hydrogen atom. A particular subject of the present invention is the products of formula (I) in which the first asymmetrical centre ① is preferably in R form, the second centre ② can preferably be in racemic or enantiomeric R or S form.

A particular subject of the present invention is the products of formula (I) as defined above, in which $R_1$, $R_2$, and n2 have the meanings indicated above, n1 represents the integer 1, and A represent the free, salified, esterified ou amidified carboxy radical or an alkyl radical, containing at most 10 carbon atoms and substituted by a radical chosen from the free, salified, esterified ou amidified carboxy radicals, optionally protected hydroxyl radicals, alkoxy radicals containing at most 4 carbon atoms, and the phenoxy radical, said products of formula (I) being in all possible racemic, enantiomeric and diastereoisomeric isomer forms, as well as the addition salts with mineral and organic acids or with mineral and organic bases of said products of formula (I).

A more particular subject of the present invention is the products de formula (I) as defined above, in which $R_1$ represents a phenyl or biphenyl radical, optionally substituted by a halogen atom, or by a hydroxyl radical optionally in the form of the trifluoromethyl-sulphonyloxy radical, n1 represents the integer 1, n2 represents the integer 0, $R_2$ represents a hydrogen atom or a methyl radical substituted by a phenyl radical, itself optionally substituted by a thienyl or phenyl radical itself optionally substituted by a cyano radical, A represents the free, salified, esterified ou amidified carboxy radical or an alkyl radical, containing at most 10 carbon atoms substituted by a phenoxy radical, said products of formula (I) being in all possible racemic, enantiomeric and diastereoisomeric isomer forms, as well as the addition salts with mineral and organic bases of said products of formula (I).

In particular, $R_1$ can represent a phenyl or biphenyl radical, optionally substituted by a bromine atom.

A quite particular subject of the present invention is the products de formula (I) as defined above, the names of which follow:

[S-(R*,S*)]N-[1-(mercaptomethyl)-2-phenylethyl]-alpha-[[(phenylmethoxy) carbonyl]amino]-1H-indole-3-propanamide, 2'-cyano-alpha-[[[1-(mercaptomethyl)-2-phenylethyl]amino]carbonyl](1,1'-biphenyl)-4-propanoic acid, (R)N-(1-mercaptomethyl)-2-phenylethyl)-11-phenoxy-undecanamide, said products of formula (I) being in all possible racemic, enantiomeric and diastereoisomeric isomer forms, as well as the addition salts with mineral and organic bases of said products of formula (I).

A subject of the present invention is also the preparation process for the products of formula (I), such as defined above, characterized in that a product of formula (II)

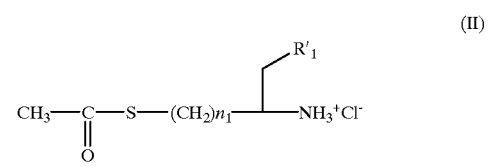

in which n1 has the meaning indicated above and $R'_1$ has the meaning indicated above for $R_1$ in which the optional reactive functions are optionally protected, is subjected either to the action of a compound of formula (III):

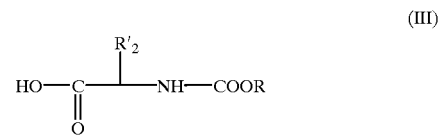

in which $R'_2$ has the meaning indicated above for $R_2$ in which the optional reactive functions are optionally protected, and R represents an alkyl or arylalkyl radical, in order to obtain the product of formula (IV):

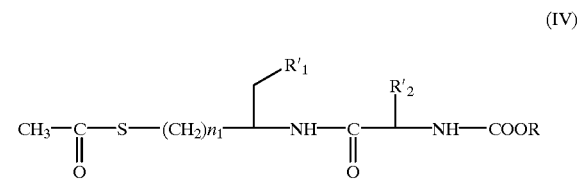

in which n1, $R'_1$, $R'_2$ and R have the meanings indicated above, or to the action of an acid halide of formula (V):

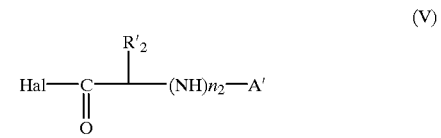

in which n2 has the meaning indicated above, Hal represents a halogen atom, $R'_2$ has the meaning indicated above and A' has the meaning indicated above for A in which the optional reactive functions are optionally protected, such as in particular A' does not represent a free carboxy radical, in order to obtain a product of formula (VI):

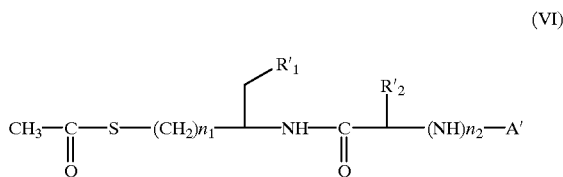

(VI)

in which n1, n2, R'$_1$, R'$_2$ and A' have the meanings indicated above,
which products of formula (IV) and (VI), in order to obtain products of formula (I) or to convert the products of formula (I) into other products of formula (I), can be treated, if desired and if necessary, to one or more of the following reactions, in any order:

a saponification reaction of the ester function into an acid function, a conversion reaction of the cyano function or amide function into an acid or tetrazolyl function, a conversion reaction of the alkoxy function into the hydroxyl function, an esterification, salification or amidification reaction of the acid function, a reaction which releases the thiol function from the

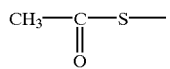

an elimination reaction of the protective groups which can be carried by the protected reactive functions, a salification reaction by a mineral or organic acid or base in order to obtain the corresponding salt, said products of formula (I) thus obtained being in all possible racemic, enantiomeric and diastereoisomeric isomer forms.

Under the preferred conditions for implementing the invention, the process described above can be carried out in the following fashion:

the reaction of the product of formula (I) as defined above with the product of formula (III) as defined above is preferably carried out with a coupling agent such as for example EDC in methylene chloride or also BOP methyl cyanide in the presence of triethylamine, or also DDC, the reaction of the product of formula (II) as defined above with the product of formula (V) as defined above is preferably carried out, in methylene chloride in the presence of pyridine. In the compound of formula (V), the halogen atom is preferably a chlorine atom.

According to the values of R'$_1$, R'$_2$ and A', the products of formulae (IV) and (VI) constitute or do not constitute products of formula (I) and can produce products of formula (I), or be converted into other products of formula (I) by being subjected to one or more of the reactions indicated above which can be carried out, for example, as indicated hereafter.

The various reactive functions which can be carried by certain compounds of the reactions defined above can, if necessary, be protected: it is for example the hydroxyl or free carboxy radicals which can be protected by the appropriate protective groups.

The following non-exhaustive list, of examples of the protection of reactive functions can be mentioned:

the amine groups can be protected in the form of other carbamates, such as those known in the chemistry of peptides, the hydroxyl groups can be protected for example by alkyl radicals such as tert-butyl, trimethylsilyl, tert-butyldimethylsilyl, methoxymethyl, tetrahydropyrannyl, benzyl or acetyl.

The products described above can, if desired, be the object, on the optional carboxy functions, of esterification, salification or amidification reactions, which can be carried out according the usual methods known to a person skilled in the art.

The acid functions of the products described above can be, if desired, amidified by a primary or secondary amine for example in methylene chloride in the presence of, for example, 1-ethyl-3-(dimethylaminopropyl) carbodiimide hydrochloride at ambient temperature.

The acid functions acid can be protected for example in the form of esters formed with easily cleavable esters such as benzylic or ter butylic esters or esters known in the chemistry of the peptides.

The optional saponification reactions of the ester function into an acid function of the products described above can, if desired, be carried out under the usual conditions known to a person skilled in the art in particular by acid or alkaline hydrolysis for example with soda or potash in alcoholic medium such as, for example, in methanol or also with hydrochloric or sulphuric acid.

The optional cyano functions of the products described above can, if desired, be converted into an acid function under the usual conditions known to a person skilled in the art for example by a double hydrolysis carried out in acid medium such as for example in a sulphuric acid, glacial acetic acid and water mixture, these three compounds preferably being in equal proportions, or also in a soda, ethanol and water mixture under reflux.

The optional cyano functions of the products described above can, if desired, be converted into the tetrazolyl function under the usual conditions known to a person skilled in the art such as for example by the cycloaddition of a metal azide such as for example sodium azide or trialkyltin azide on the nitrile function as indicated in the method described in the article referenced as follows: J. Organometallic Chemistry., 33, 337 (1971) KOZIMA S.and al.

The acid functions can be converted into tetrazole as indicated in the publication Bio. Med. Chem. Leh. 1995, 145.

The optional alkoxy functions such as in particular methoxy of the products described above can, if desired, be converted into the hydroxyl function under the usual conditions known to a person skilled in the art for example with boron tribromide in a solvent such as for example methylene chloride, with pyridine hydrobromide or hydrochloride or also with hydrobromic or hydrochloric acid in water or trifluoroacetic acid under reflux.

The optional hydroxyl functions of the products described above can, if desired, be converted into an acid function by oxidation under the usual conditions known to a person skilled in the art in the conditions such as for example by the action of Jones reagent to access the acids.

The elimination of the protective groups such as for example those indicated above can be carried out under the usual conditions known to a person skilled in the art in particular by an acid hydrolysis carried out with an acid such as hydrochloric, benzene sulphonic or paratoluene sulphonic, formic or trifluoroacetic acid or also by catalytic hydrogenation.

The phthalimido group can be eliminated with hydrazine.

A list of the different protective groups that can be used will be found for example in the Patent BF 2 499 995.

The products described above can, if desired, be the object of salification reactions for example with a mineral or organic acid or with a mineral or organic base according to the usual methods known to a person skilled in the art.

The optional optically active forms of the products described above can be prepared by resolution of the racemics according to the usual methods known to a person skilled in the art.

Illustrations of such reactions defined above are given in the preparation of the examples described hereafter.

The structures and properties of endothelin and of its precursor Big Endothelin are described in the literature such as for example in the document WO 93/11154.

The products of formula (I) of the present invention have been found to have an inhibitory activity on the enothelin-converting enzyme which allows the properly so-called endothelin to be obtained from Big Endothelin, which is thus an extremely powerful vasoconstrictor agent.

The products of formula (I) of the present invention can therefore be used in the treatment of illnesses resulting from abnormally high quantities of endothelin.

The compounds of formula (I) as defined above as well as their addition salts as defined above have useful pharmacological properties.

The products of formula (I) as defined above, endowed with inhibitory properties of the endothelin-converting enzyme, can thus in particular reduce the quantities and therefore the effects of endothelin, in particular the vasoconstrictor and hypertensor effects induced by endothelin. In particular an antiischemic effect is noted.

The products of formula (I) therefore also have the effect of reducing the stimulating effects of endothelin at the level of all cell types, in particular the smooth muscle cells, the fibroblasts, the neuronal cells and the bone cells.

These properties justify their use in therapeutics and a particular subject of the invention is as medicaments, the products of formula (I), said products of formula (I) being in all possible racemic, enantiomeric and diastereoisomeric isomer forms, as well as the addition salts with pharmaceutically acceptable mineral and organic acids or with pharmaceutically acceptable mineral and organic bases of said products of formula (I).

More particularly a subject of the invention is also, as medicaments, the preferred products as defined by formula (I) above in which;

$R_1$ represents a phenyl or biphenyl radical, optionally substituted by halogen atom, n1 represents the integer 1, n2 represents the integer 0, $R_2$ represents a hydrogen atom or a methyl radical substituted by a phenyl radical, itself optionally substituted by a thienyl or phenyl radical itself optionally substituted by a cyano radical, A represents the free, salified, esterified or amidified carboxy radical or an alkyl radical, containing at most 10 carbon atoms substituted by a phenoxy radical, said products of formula (I) being in all possible racemic, or optically active isomer forms, as well as the addition salts with pharmaceutically acceptable mineral and organic acids or with pharmaceutically acceptable mineral and organic bases of said products of formula (I).

A quite particular subject of the invention is, as medicaments, the products described hereafter in the examples and in particular the products of formula (I) as defined above, the names of which follow:

[S-(R*,S*)]N-[1-(mercaptomethyl)-2-phenylethyl]-alpha-[[(phenylmethoxy) carbonyl]amino]-1H-indole-3-propanamide, 2'-cyano-alpha-[[[1-(mercaptomethyl)-2-phenylethyl]amino]carbonyl](1,1'-biphenyl)-4-propanoic acid, (R)N-(1-mercaptomethyl)-2-phenylethyl)-11-phenoxy-undecanamide, as well as the addition salts with pharmaceutically acceptable mineral and organic bases of said products of formula (I).

The medicaments, which are a subject of the invention, therefore find their use in the treatment, by use of an inhibitory agent of the endothelin-converting enzyme, for illnesses such as, for example, vascular spasms, vasospasm as a result of a cerebral haemorrhage, coronary spasms, peripheral vascular spasms as well as renal insufficiencies. These medicaments can also be used in the treatment of myocardial infarction, of congestive cardiac insufficiency, in the prevention of post-angioplasty recurrence of stenosis, of cardiac and vascular fibrosis, in the treatment of atherosclerosis, of certain forms of hypertension such as in particular pulmonary hypertension, as well as in the treatment of asthma.

The medicaments, which are a subject of the invention, can also find a use in the treatment of osteoporosis, prostatic hypertrophia and as neuronal protectors.

The invention extends to the pharmaceutical compositions containing as active ingredient at least one of the medicaments as defined above.

These pharmaceutical compositions can be administered by buccal, rectal route, by parenteral route or by local route as a topical application on the skin and mucous membranes or by injection by intravenous or intramuscular route.

These compositions can be solid or liquid and be presented in all the pharmaceutical forms commonly used in human medicine, such as for example, plain or sugar-coated tablets, capsules, granules, suppositories, injectable preparations, ointments, creams, gels and aerosol preparations; they are prepared according to the usual methods. The active ingredient can be incorporated with excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents, preservatives.

The usual dose, variable according the product used, the patient treated and the illness in question, can be, for example, from 1 to 300 mg per day in an adult, by oral route or from 1 to 100 mg per day by intravenous route.

Certain starting products of formula (II), (III) and (V) are known, may be commercially available or prepared according to the usual methods known to a person skilled in the art or also for example as indicated in the European Patent EP 0465369.

In particular certain products of formula (II) can also be prepared from other products of formula (II) for example by subjecting them to one or more of the reactions described above, carried out under the conditions also described above.

Preparations for the compounds of formula (II) are indicated in the examples described hereafter.

It should be noted that the compound of formula (II) can be in racemic or optically pure form and that, consequently, the product of formula (IV) obtained can also be in racemic or optically pure form.

The compound of formula (II) in which ni represents the integer 1 and R'₁ represents the phenyl radical can be prepared as indicated in Preparation 1E of EP 0465369, either starting with the amino acid L-phenylalamine in order to produce the product of formula (II) of form S, or starting with the amino acid D-phenylalamine in order to produce the product of formula (II) of form R, or starting with a mixture of amino acids, L- and D-phenylalamine in order to produce the product of formula (II) of racemic form: these compounds of formula (II) thus obtained produce respectively, after reaction with the compound of formula (III), a product of formula (IV) which will be respectively in ① in S form (Example 1), in R form (Example 2) or in racemic form (Example 5).

Other compounds of formula (II), can be obtained in the same fashion starting from other amino acids.

In particular, the products of formula (II) in which R'₁ represents the biphenyl radical can be obtained starting from tyrosine.

Such a reaction is indicated in the preparation of Example 7, described hereafter.

Other compounds of formula (II), in which n1 represents the integer 0 can be prepared starting from the corresponding acid in order to produce by a Curtius reaction described in the literature, the sought amine.

The compounds of formula (III) represent amino acids which can be substituted on the nitrogen: such compounds of formula (III) may be commercially available or be prepared according to the usual methods known to a person skilled in the art.

The compounds of formula (V) are preferably acid chlorides prepared from the corresponding acid itself commercially available or prepared according to the usual methods known to a person skilled in the art, such as by condensation of an alkyl halide on a malonate.

Finally, a subject of the present invention is, as new industrial products, the compounds of formulae (IV) and (VI) as defined above.

Particularly a subject of the present invention is the use of the products of formula (I) as defined above, for the preparation of an inhibitory agent of the endothelin-converting enzyme.

Therefore a particular subject of the present invention is the use of the products of formula (I) as defined above, for the preparation pharmaceutical compositions intended for the treatment, by inhibition of the endothelin-converting enzyme, for illnesses such as, in particular, hypertension induced by endothelin, vascular spasms, the effects of a cerebral haemorrhage, renal insufficiencies, myocardial infarction , cardiac insufficiency as well as the prevention of post-angioplasty recurrence of stenosis and cardiac and vascular fibrosis.

The following examples illustrate the invention without however limiting it.

EXAMPLE 1

[S-N-(1-Mercaptomethyl)-2-phenylethyl)-2-(((phenylmethoxy) carbonyl)amino)-indole-3-propanamide STAGE 1
[-(R*,R*)]N-[1-[(Acetylthio)methyl)-2-phenyl-ethyl]-alpha-[[(phenylmethoxy)carbonyl]amino]-1H-indole-3-propanamide 183 mg of 1-(3-dimethylamino propyl)3-ethyl carbodiimide hydrochloride is introduced into 10 ml of methylene chloride and 120 µl of triethylamine is added. Agitation is carried out for 10 minutes at ambient temperature and 300 mg of N-carbobenzyloxy Triptomane (NCBz Trp) is added. The reaction medium is again left for 10 minutes at ambient temperature then in one go 200 mg of the amine hydrochloride in S form is added, prepared as indicated in Preparation 1E of EP 0465369 with L-phenylalamine as starting product. The reaction is agitated for 4 hours at ambient temperature, followed by evaporating, taking up in 30 ml of ethyl acetate and washing twice with 0.1N hydrochloric acid, then with salt water (twice). After chromatography on silica with ethyl acetate-hexane: 50—50 as eluant, 270 mg of expected product is obtained.

STAGE 2
[S-N-(1-Mercaptomethyl)-2-phenylethyl)-2-(((phenylmethoxy) Carbonyl)amino)-indole-3-propanamide 120 mg of product obtained in Stage 1 above is introduced into 3 ml of methanol. Then 0.34 ml of 1N soda is added and the reaction medium is left for 1 hour at 0° C. After taking up in 4 ml of water, acidification is carried out with 1N hydrochloric acid until a pH approx.=½ and the precipitate formed is filtered off. After drying, 120 mg of expected product is obtained. M.p.=164° C. Rotatory power $\alpha_D$ at a concentration of 0.5 in methanol=−20.8°.

ANALYSES IR (CHCl₃) cm⁻¹

| | |
|---|---|
| =C—NH | 3477–3420 |
| >=O | 1716–1673 |
| SH | 2570 |
| Aromatic | |
| C=C | 1620–1578–1585–1497 |

Amide II
NMR (250 MHz 1H, CDCl₃) 0.81 (t, 1H,SH); 2.09 to 2.37 (m, CHCH₂—SH) −2.64 (d, 2H, CH₂); 3.11 (dd, 1H,CH₂); 3.32 (dd, 1H); 4.20 (m 1H); 4.45 (n, 1H); 5.12 (s, 2H, O—CH₂-ph); 5.43 (d, 1H,NH); 5.75 (d, 1H,NH); 6.96 to 7.66 (n, 14H); 8.07 (ws, 1H, indole NH).

EXAMPLE 2

[(R*,S*)]-N-[1-(Mercaptomethyl)-2-phenylethyl]-alpha-[[(phenylmethoxy) carbonyl)amino)-1H-indole-3-propanamide The operation is carried out as in Example 1 using in Stage 1 the amine hydrochloride in R form prepared as indicated in Preparation 1E of EP 0465369 with as starting product D-phenylalamine. In this way 120 mg of expected product is obtained.

Rotatory power $\alpha_D$ at a concentration of 0.75 in chloroform=+8.50°.

ANALYSES
NMR (1H, CDCl₃, 250 MHz, δ ppm) 1.04 (t, 1H,SH); 2.3 to 2.7 (m, 4H, 2×CH₂); 3.11 (dd, 1H); 3.34 (dd, 1H); 4.18 (m, 1H,CH—CH₂); 4.44 (m, 1H,CH—NHCHO); 5.11 (s, 2H, CH₂ ph); 5.40 (d, 1H,NH); 5.75 (d, 1H,NH); 8.02 (s, 1H, indole NH); 6.95 (n, 3H, aromatic H); 7.10 to 7.4 (n, 11H, aromatics H's); 7.66 (wd, 1H, aromatics).

EXAMPLE 3

[S-(R*,R*)]-2-(((1,1-Dimethylethoxy) carbonyl) amino)-N-(l-(mercaptomethyl)-2-phenylethyl)-indole-3-propanamide STAGE 1
[S-(R*,R*)]-N-[1-((Acetylthio)methyl]-2-phenylethyl]-alpha-[[(1,1-dimethylethoxy) carbonyl)amino]-1H-indole-3-propanamide The operation is carried out as in Stage 1 of Example 1 using N-BOC-tryptophan (N-terbutyloxycarbonyl-Trp) instead of N-CBZ-tryptophan (N-carbobenzyloxy-Trp). In this way 270 mg of expected product is obtained.

STAGE 2

[S-(R*,R*)]]-2-(((1,1-Dimethylethoxy)carbonyl) amino)-N-(1-(mercaptomethyl)-2-phenylethyl)-indole-3-propanamide The operation is carried out as in Stage 2 of Example 1 and in this way 120 mg of expected product is obtained. M.p.=77° C.

Rotatory power $\alpha_D$ at a concentration of 0.5 in methanol=−22.4°

ANALYSES

NMR (1H, CDCl$_3$, 250 MHz, δ ppm) 0.87 (t, 1H,SH); 1.44 (s, 9H, tbu); 2.26 (m, CH$_2$,2H); 2.65 (m, 2H,CH$_2$-ph); 3.10 (dd, 1H,CH$_2$); 3.30 (dd, 1H,CH$_2$); 4.22 (m, 1, 1H,CH); 4.39 (m, CH,LH); 5.13 (d, 1H,NH); 5.84 (d, 1H,NH); 6.99 (s, 1H,H$_2$ indole); 7 to 7.22 (m, 7H); 7.36 (d, 1H,Ar); 7.67 (s, 1H,Ar); 8.04 (ws, 1H,NH indole). IR (CHCl$_3$) cm$^{-1}$

| | |
|---|---|
| =C—NH | 3477–3420 |
| >=O | 1706–1672 |
| SH | 2570 |
| Conjugated syst. | |
| Amide II + | 1620–1605–1513–1496–1490 |
| Aromatic | |
| Me of tBu | 1368 |

EXAMPLE 4

2'-cyano-alpha-[[[1-(mercaptomethyl)-2-phenylethyl]amino]carbonyl]-(1,1'-biphenyl)-4-propanoic acid STAGE 1
2'-cyano-alpha-(ethoxycarbonyl)-(1,1'-biphenyl)-4-propanoyl chloride 105 mg of sodium hydride at 60% in oil, washed twice beforehand with pentane, is introduced into 15 ml of tetrahydrofuran and placed at 0° C. under argon. A solution of 0.5 ml of terbutyl ethyl malonate is added dropwise to 1 ml of tetrahydrofuran and the whole is left for 30 minutes at ambient temperature then returned to 0° C. and a solution of 410 mg of 4'-(bromomethyl)-(1,1'-biphenyl)-2-carbonitrile prepared as indicated in EP 0465368 (Example 49) is added dropwise. The solution is agitated for 1 hour at 0° C. and for 3 hours at ambient temperature, then acidified with 1N hydrochloric acid to a pH~2.Then extraction is carried out with ethyl acetate followed by drying. After chromatography on silica with ethyl acetate—cyclohexane: 25–75 as eluant, 400 mg of an oil is obtained which is taken up in 10 ml of methylene chloride. 10 ml of trifluoroacetic acid is added and the whole is left for 3 hours at ambient temperature then evaporation is carried out. The oily residue is taken up in 10 ml of thionyl chloride and left under agitation overnight. After evaporation of the thionyl chloride, the expected acid chloride is obtained used as it is in the following stage.

STAGE 2
Ethyl [R-(R*,R*)] and (R-(R*,S*)]alpha-[[[1-((acetylthio) methyl]-2-phenylethyl]amino]carbonyl)-2'-cyano-(1, 1'-biphenyl)-4-propanoate 10 ml of methylene chloride is added to the product obtained in Stage 1 above and, after having taken the reaction medium to reflux, 377 mg of the amine hydrochloride obtained in Preparation 1E of EP 0465369 is added. Then a few drops of pyridine is added in order to obtain a pH~4–6 and agitation is carried out under reflux for 4 hours.

The solution is then evaporated and after chromatography on silica with ethyl acetate—cyclohexane—methylene chloride: 25-25-50 as eluant, 400 mg of expected product is obtained.

Analyses

NMR (1H, CDCL$_3$, 200 MHz) 1.2 (2t, 3H, CH$_3$); 2.4 and 2.45 (2s, 3H, SAc); 2.7–3.5 (m, 7H); 4.2 (m, 2H, CO$_2$CH$_2$); 4.4 (m, 1H, OC—CH—CO); 6.55 and 6.65 (2d, 1H, NH); 7.1 to 7.6 (m, 11H); 7.7 (d, 1H, Ar); 7.9 (d, 1H, Ar).

STAGE 3
2'-Cyano-alpha-[[[1-(mercaptomethyl)-2-phenylethyl]amino]carbonyl]-(1,1'-biphenyl)-4-propanoic Acid 400 mg of product obtained in Stage 2 above is introduced into 5 ml of tetrahydrofuran and 2.5 ml of water is added. Then 115 mg of lithium hydroxide is added at ambient temperature and the whole is left under agitation for 2 hours.

The reaction is then acidified by the addition of 1N hydrochloric acid to pH~2,then, after the addition of 5 ml of H$_2$O, extraction is carried out three times with methylene chloride+10% of methanol.

After drying and evaporation, chromatography is carried out on silica with methylene chloride—methanol: 90–10 as eluant and 280 mg of expected product (white foam) is obtained in the form of a mixture of 2 diastereoisomers. Tgum~130° C.

Analyses:

NMR (DMSO, 300 MHz, δ ppm) 1.98 (m, SH); 2.4 to 3.3 (m, 7H); 3.93 and 4.02 (m, 1H, OC—CH—CO); 7.08 to 7.32 (m, 7H, Ar); 7.41 (m, 2H, Ar); 7.55 (m, 2H, Ar); 7.77 (m, 1H); 7.92 (d, 1H, Ar); 8.32 and 8.38 (wd, 1H, CONH).

EXAMPLE 5

(S) Alpha-(((1-(mercaptomethyl)-2-phenylethyl) Amino) Carbonyl) Benzenepropanoic Acid STAGE 1
Alpha-(ethoxycarbonyl)-benzenepropanoyl Chloride The operation is carried out as in Stage 1 of Example 4 using benzyl bromide (commercial) instead of 4'-(bromomethyl) (1,1'-biphenyl) 2-carbonitrile and in this way the expected product is obtained.

STAGE 2
Ethyl [S-(R*,S*)] and (S-(R*,S*)]alpha-[[[1-[(acetylthio) Methyl]-2-phenylethyl] Amino]carbonyl]-benzenepropanoate The operation is carried out as in Stage 2 of Example 4 and in this way the expected product is obtained.

STAGE 3
(S) Alpha-(((1-(mercaptomethyl)-2-phenylethyl) amino) carbonyl)benzenepropanoic Acid The operation is carried out as in Stage 3 of Example 4 and in this way the expected product is obtained. M.p.= 65–70° C.;

Analyses:

NMR (DMSO, 300 MHz, δ ppm) Mixture of 2 diastereoisomers (S,R) and (S,S) 1.75 and 2.22 (wt, SH); 2.3 to 4.5 (m, 8H); 7 to 7.30 (m, 10H); 8.09 and 8.56 (d, 1H, CONH); 12.52 (wide m, COOH).

EXAMPLE 6

(R) N-(1-Mercaptomethyl)-2-phenylethyl)-11-phenoxy-undecanamide

STAGE 1
11-phenoxy-undecanoyl Chloride 250 mg of 11-phenoxy undecanoic acid (commercial) is mixed with 2 ml of pure thionyl chloride and the whole is left overnight at ambient temperature. In this way 265 mg of expected product is obtained.

STAGE 2

(R) N-[1-[(Acetylthio) methyl]-2-phenylethyl]-11-phenoxy-undecanamide

The operation is carried out as in Stage 2 of Example 4 starting with 265 mg of the product obtained in Stage 1 above and 120 mg of the amine hydrochloride (R form) obtained in Preparation 1E of EP 0465369.In this way 150 mg of expected product is obtained.

STAGE 3

N-(1-Mercaptomethyl)-2-phenylethyl) 11-phenoxy-undecanamide 100 mg of the product obtained in Stage 2 above is introduced into 4 ml of methanol and 120 µl of 2N soda is added at 0° C. The whole is agitated for 1 hour at 0° C. Then 10 ml of water is added, the white precipitate which forms is filtered out and dried. In this way 70 mg of expected product is obtained. M.p.=65° C.

NMR (CDCl$_3$, 300 MHz, δ ppm); 1.20 to 1.82 (m, 17H); 2.14 (t, COCH$_2$); 2.66 (m, AB/sys resolved, CH$_2$CH$_2$SH); 2.88 (m, ph-CH$_2$CH); 3.95 (t, CH$_2$-CH$_2$-OPh); 4.37 (m, CH$_2$-CH(NH)CH$_2$); 5.55 (d, NHCO); 6.85 to 6.97 (m, 2H); 7.16 to 7.35 (m, 8H).

EXAMPLE 7

2'-cyano-alpha-[[[1-(mercaptomethyl) 2-biphenylethyl]amino]carbonyl]-(1,1'-biphenyl)-4-propanoic Acid The operation is carried out as in Example 4,taking as starting product the amine hydrochloride in which R$_1$ represent biphenyl, instead of the amine hydrochloride in which R$_1$ represent phenyl, prepared by using as starting product the product (R)-α-[[(1,1-dimethylethoxy)carbonyl]amino) (1,1'-biphenyl ]-4-propanoic acid, which here is in the R form and which is prepared as its enantiomer of S form the preparation of whch is described in the following reference: Journal of Medecinal Chemistry, 1995, Vol. 38, 1689,then by preparing the corresponding hydrochloride as indicated in Stage D of EP 0465369. In this way the expected product of Example 7 is obtained.

By proceeding as in Examples 4 and 7 described above, using, if appropriate, instead of 4'-(bromo-methyl) (1,1'-biphenyl) 2-carbonitrile, 4'-2-thienyl benzyl bromide, prepared according to the process described in the following reference: Journal of Medicinal Chemistry 38, 2357, 1995, using the 2-thienyl boronic as arylboronic, in this way the following products of Examples 8, 9 and 10 are obtained:

EXAMPLE 8

[[(1-(Mercaptomethyl)-2-biphenylethyl]amino] carbonyl ]-(1,1'-thienylphenyl)-4-propanoic acid Analyses:

MS: (M-CO$_2$)H$^+$:458

EXAMPLE 9

([[[1- (Mercaptomethyl) 2-phenylethyl]amino] carbonyl ](1,1'-thienylphenyl) 4-propanoic acid

EXAMPLE 10

2'-Cyano-alpha-[[[1-(mercaptomethyl) 2-(paratrifluoromethylsulphonyloxy) phenylethyl] amino]carbonyl](1,1'-biphenyl) 4-propanoic acid Analyses:

NMR (DMSO) 2.6 to 3.2 (7H); 3.92 and 4.04 (m, 1H); 7.06 to 7.95 (Ar) 8.25 and 8.4 (1H,NH).

EXAMPLE 11 OF PHARMACEUTICAL COMPOSITION

Tablets corresponding to the following formula were prepared:

| | |
|---|---|
| Product of Example 4 | 50 mg |
| Excipient for a tablet completed at | 200 mg |

(detail of excipient: lactose, talc, starch, magnesium stearate).

PHARMACOLOGICAL RESULTS

Determination of the Inhibitory Effect of the Endothelin-converting Enzyme (ECE)

A test is used, in which the product (2,3-$^3$H)propionyl-b-ET-1(19–35) prepared as indicated below in a) is cleaved by ECE into the product (2,3-$^3$H)propionyl-b-ET-1(19–21) in the presence of product P of which the inhibitory activity of ECE one wishes to determine as indicated below in b): the inhibitory activity of ECE of the product P will therefore be accordingly as high as the quantity of product of formula (II) formed, determined by counting the radioactivity, will be low. The operation is carried out as follows:

a)—Preparation of Tritiated Peptide (2,3-$^3$H)Propionyl-b-ET-1 (19–35)

N-succinimidyl- (2, 3-$^3$H)-propionate (Amersham code TRK.556) is in solution in 5 ml of toluene at 1 mCi/ml, 99 mCi/mmol==>5 mCi and 50 nmoles.

The toluene is evaporated off until a solution of 10 µl is obtained then 25 µl of a solution of DMSO containing 0.2 mg of b-ET-1(19–35) is added, b-ET-1(19–35) (MW= 2014.2) having previously been dried over potash overnight. Evaporation is continued for 10 minutes then the solution is agitated under a stream of nitrogen for 15 minutes in order to eliminate the residual toluene.

Agitation is then gently carried out for 4 days.

To purify, 225 µl of phosphate buffer pH 6.5 and 50 µl of acetonitrile are added then agitation is carried out for 10 minutes and the radioactive solution obtained is separated into 2 injections of 150 µl on a Nucleosil C$_{18}$ column (150×4.6 mm).

Elution is carried out with a flow rate of 0.8 ml/mn with a gradient of 0 to 20% of acetonitrile over 20 minutes then 20 to 35% over 50 minutes.

Analyses:

Analysis of the fractions is carried out by counting the tritium with a liquid scintillation counter (1 µl in 5 ml of scintillating HiSafe3) for 60 seconds.

The radioactive fractions are combined and fractionated into 200 µl samples in siliconized Eppendorf tubes which can be stored at −80° C. or −20° C.

Characteristics of the Product Obtained:

dpm=1 067 274 560 corresponding to 0.5 mCi. Radioactive yield: 10%. Specific activity: (99×10)/30.5=32.5 Ci/mmol.

b)—Determination of the Inhibitory Activity of the Endothelin-converting Enzyme (ECE)

10 µl of ECE i.e. 1 to 2 µg of purified ECE are pre-incubated for 30 minutes at 37° C., in 400 µl of a 50 mM Tris maleate buffer pH=6.5, 20 µl of 5M sodium chloride and 5 µl of product P the inhibitory activity of which one wishes to test, in solution at different concentrations (comprised between 1 µM at 100 mM) (i.e. final concentrations in product P of 10 nM to 1 mM).

The reaction is initiated by the addition of 10 μl of (2,3-³H)propionyl-b-ET-1(19–35) prepared as indicated above in a), at a final concentration of $1.8.10^{-12}$M.

After incubation for one hour at 37° C., the reaction is stopped by the addition of 600 μl of ethyl acetate and the (2,3-³H)propionyl-b-ET-1(19–21) is extracted by mechanical agitation for 2 minutes.

300 μl of the organic phase is removed, 5 ml of liquid scintillator is added and the radioactivity is counted for 1 minute with a liquid scintillation counter.

Each measurement is carried out in triplicate except for the ECE control (control enzyme, without the product the ECE inhibitory activity of which one wishes to test), for which the measurement is carried out six times.

The percentage inhibition is calculated by establishing the relationship:

$$\frac{\text{tested product} - \text{blank}}{\text{control enzyme} - \text{blank}}$$

The blank is carried out starting with the solution obtained without enzyme.

The test was validated by its application to known inhibitors i.e. P1 which is phosphoramidon and P2 which is N-(phenylethylphosphonyl)-Leu-Trp (TAKEDA).

The table below gives the results obtained by using as P products the products in the examples in the present invention, the ECE inhibitory activities of which one wishes to test.

From the cpm's obtained and by plotting the graph of the percentage of inhibition relative to the concentration of inhibitor (nM), the $IC_{50}$ is calculated which therefore corresponds to the concentration which causes a 50% inhibition of ECE.

The numbered results obtained are indicated in the table below:

| Products of Examples | $IC_{50}$ (nM) |
|---|---|
| 4 | 30 |
| 6 | 220 |
| 10 | 150 |

What is claimed is:

1. A method of treating vasoconstrictor and hypertension effects in warm-blooded animals comprising administering to warm-blooded animals an amount sufficient to inhibit vasoconstrictor and hypertension effects of a compound of the formula

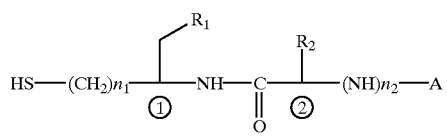

I wherein $R_1$ is unsubstituted or substituted phenyl or biphenyl, the substituents being at least one member of the group consisting of hydroxy, protected hydroxy, alkoxy of 1 to 4 carbon atoms, —CN, carboxy, salified carboxy, carboxy esterified with alkanol of up to 6 carbon atoms, amidified carboxy, benzyloxy and dioxol, $n_1$ and $n_2$ are individually 0 or 1, $R_2$ is hydrogen or methyl substituted with a member of the group consisting of phenyl, phenylthio and indolyl, all unsubstituted or substituted by phenyl or substituted with at least one member of the group consisting of a) halogen, —OH, protected —OH, —CN, alkoxy of 1 to 4 carbon atoms, carboxy, salified carboxy, carboxy esterified with alkanol of 1 to 6 carbon atoms, amidified carboxy, benzyloxy and b) thienyl, naphthyl and phenyl, each unsubstituted or substituted with at least one member of the group consisting of halogen, —OH, protected —OH, alkoxy of 1 to 4 carbon atoms, —CN, carboxy, salified carboxy, carboxy esterified with alkanol of 1 to 6 carbon atoms and amidified carboxy, A is selected from the group consisting of carboxy, salified carboxy, carboxy esterified with an alkanol of 1 to 6 carbon atoms, amidified carboxy, tetrazolyl, salified tetrazolyl and alkyl of 1 to 10 carbon atoms substituted with a member selected from the group consisting of a) carboxy, salified carboxy, carboxy esterified with an alkanol of 1 to 6 carbon atoms, amidified carboxy, —OH, protected —OH, alkoxy of 1 to 4 carbon atoms, and b) phenoxy, phenyl, naphthyl, thienyl, indolyl and pyridyl, each unsubstituted or substituted with at least one member of the group consisting of halogen, —OH, protected —OH, alkoxy of 1 to 4 carbon atoms, —CN, carboxy, salified carboxy, carboxy esterified with an alkanol of 1 to 6 carbon atoms and amidified carboxy, 1) and 2) indicating possible asymmetric centers and its addition salts with a non-toxic, pharmaceutically acceptable acid or base.

2. The method of claim 1 wherein $n_1$ is 1 and it is selected from the group consisting of carboxy, salified carboxy, carboxy esterified with an alkanol of 1 to 6 carbon atoms, amidified carboxy and alkyl of 1 to 10 carbon atoms substituted by a member selected from the group consisting of carboxy, salified carboxy, carboxy esterified with an alkanol of 1 to 6 carbon atoms, amidified carboxy, —OH, protected —OH, alkoxy of 1 to 4 carbon atoms and phenoxy.

3. The method of claim 1 wherein $R_1$ is phenyl or biphenyl, both unsubstituted or substituted with a member selected from the group consisting of halogen, —OH and trifluoromethyl sulfonyloxy, $n_1$ is 1, $n_2$ is 0, $R_2$ is hydrogen or methyl substituted with a member of the group consisting of thienyl, phenyl and cyanophenyl and A is selected from the group consisting of carboxy, salified carboxy, carboxy esterified with an alkanol of 1 to 6 carbon atoms, amidified carboxy and alkyl of 1 to 10 carbon atoms substituted with phenoxy.

* * * * *